United States Patent [19]

Herrnstadt et al.

[11] Patent Number: 4,853,331

[45] Date of Patent: * Aug. 1, 1989

[54] CLONING AND EXPRESSION OF *BACILLUS THURINGIENSIS* TOXIN GENE TOXIC TO BEETLES OF THE ORDER COLEOPTERA

[75] Inventors: Corinna Herrnstadt, San Diego; Edward Wilcox, Escondido, both of Calif.

[73] Assignee: Mycogen Corporation, San Diego, Calif.

[*] Notice: The portion of the term of this patent subsequent to Sep. 13, 2005 has been disclaimed.

[21] Appl. No.: 278,292

[22] Filed: Nov. 30, 1988

Related U.S. Application Data

[60] Division of Ser. No. 219,420, Jul. 15, 1988, which is a continuation-in-part of Ser. No. 767,227, Aug. 16, 1985.

[51] Int. Cl.[4] ................... C12N 1/20; C12N 5/00; C12N 15/00; C07K 13/00
[52] U.S. Cl. .................... 435/252.1; 435/70; 435/91; 435/169; 435/170; 435/171; 435/172.3; 435/240.1; 435/254; 435/320; 435/832; 435/848; 435/874; 536/27; 530/350; 935/9; 935/24; 935/60; 935/66
[58] Field of Search ................ 435/70, 91, 170, 169, 435/171, 240.1, 172.3, 252, 254, 320, 832, 848, 874, 911; 935/22, 59, 60, 64, 66, 67, 68, 69, 70, 71, 72, 73, 74, 75; 536/27; 530/350

[56] References Cited

U.S. PATENT DOCUMENTS

4,467,036 8/1984 Schnepf et al. .................. 435/317
4,771,131 9/1988 Herrnstadt et al. ............... 536/27

OTHER PUBLICATIONS

Couch, T. L. (1980), "Mosquito Pathogenicity of *Bacillus thuringiensis* var. *israelensis*," Developements in Industrial Microbiology, 22:61–67.

Beegle, C. C. (1987), "Use of Entomogenous Bacteria in Agroecosystems," Developments in Industrial Microbiology, 20:79–104.

Krieg, A., Huger, A. M., Langenbruch, G. A., and Schnetter, W. (1983), "*Bacillus thuringiensis* var. *tereorionis*: a New Pathotype Effective Against Coleopteran Larvae," Z. Ang. Ent., 96:500–508.

*Primary Examiner*—Elizabeth C. Weimar
*Assistant Examiner*—Richard C. Peet
*Attorney, Agent, or Firm*—Roman Saliwanchik; David R. Saliwanchik

[57] ABSTRACT

The toxin gene encoding a protein toxic to beetles of the order Coleoptera, named M-7, has been cloned and expressed. M-7 is a novel *Bacillus thuringiensis* strain which has been deposited with a recognized culture repository. The microbe is now known as *B. thuringiensis* strain *san diego*.

1 Claim, No Drawings

CLONING AND EXPRESSION OF BACILLUS THURINGIENSIS TOXIN GENE TOXIC TO BEETLES OF THE ORDER COLEOPTERA

CROSS REFERENCE TO RELATED APPLICATION

This is a division of application Ser. No. 219,420, filed July 15, 1988, which is a continuation-in-part of our copending application Ser. No. 767,227, filed on Aug. 16, 1985.

BACKGROUND OF THE INVENTION

The spore-forming microorganism Bacillus thuringiensis (Bt) produces the best-known insect toxin. The toxin is a protein, designated as δ-endotoxin. It is synthesized by the Bt sporulating cell. The toxin, upon being ingested in its crystalline form by susceptible insect larvae, is transformed into biologically active moieties by the insect gut juice proteases. The primary target is insect cells of the gut epithelium, which are rapidly destroyed. Experience has shown that the activity of the Bt toxin is so high that only nanogram amounts are required to kill susceptible insect larvae.

The reported activity spectrum of Bt covers insect species within the order Lepidoptera, which is a major insect problem in agriculture and forestry. The activity spectrum also includes the insect order Diptera, wherein reside some species of mosquitoes and blackflies. See Couch, T. L., (1980) "Mosquito Pathogenicity of Bacillus thuringiensis var. israelensis," Developments in Industrial Microbiology 22:61–67; Beegle, C. C., (1978) "Use of Entomogenous Bacteria in Agroecosystems," Developments in Industrial Microbiology, 20:97–104.

Kreig et al., Z. ang. Ent. (1983) 96:500–508, describe a Bt isolate named Bacillus thuringiensis var. tenebrionis, which is reportedly active against two beetles of the order Coleoptera. These are Colorado potato beetle, Leptinotarsa decemlineata, and Agelastica alni. This is the only known Bt isolate reported to contain such activity; all previously identified Bt strains have had activity against caterpillars (order Lepidoptera) or larvae of certain flies (order Diptera).

The Krieg et al. Bt isolate is not available for side-by-side comparison with the Bt isolate used as the source of the novel Bt gene of the subject invention. Therefore, since the Krieg et al. Bt isolate is not available to the public, the Krieg et al. publication is not a valid patent law reference under U.S. law.

BRIEF SUMMARY OF THE INVENTION

Disclosed and claimed is the cloning and expression of the toxin gene toxic to beetles of the order Coleoptera. The toxin produced by the cloned gene has activity against beetles of the order Coleoptera but not against Trichoplusia ni, Spodoptera exigua or Aedes aegypti. Included in the Coleoptera are various Diabrotica species (family Chrysomelidae) that are responsible for large agricultural losses. For example, D. undecimpunctata (western spotted cucumber beetle), D. longicornis (northern corn rootworm), D. virgitera (western corn rootworm), and D. undecimpunctata howardi (southern corn rootworm).

DETAILED DISCLOSURE OF THE INVENTION

The Bacillus thuringiensis isolate used as the source of the toxin gene of the subject invention, designated "M-7," is unusual in having a unique parasporal body (crystal) which under phase contrast microscopy is dark in appearance with a flat, square configuration.

A subculture of B. thuringiensis M-7, now known as B. thuringiensis strain san diego (B.t.sd) has been deposited in the permanent collection of the Northern Regional Research Laboratory, U.S. Department of Agriculture, Peoria, Ill., U.S.A. on Feb. 27, 1985. The culture was assigned the accession number NRRL B-15939 by the repository. The deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

B. thuringiensis strain san diego, NRRL B-15939, can be cultured using standard art media and fermentation techniques. Upon completion of the fermentation cycle, the bacteria can be harvested by first separating the Bt spores and crystals from the fermentation broth by means well known in the art. The DNA (chromosomal and plasmid) from the cells can be isolated by standard procedures and purified by procedures well known in the art. For example, such standard procedures are disclosed in Maniatis et al., Molecular Cloning (1982), Cold Spring Harbor Laboratory.

The purified DNA then can be digested with a suitable restriction endonuclease.

A gene bank of B.t.sd DNA then can be constructed. In the subject invention, the purified B.t.sd DNA, obtained as described above, was digested with the restriction endonuclease BamHI and cloned into the BamHI site of the well-known and available plasmid pBR322.

Once the gene bank B.t.sd DNA was constructed, it then became necessary to construct a DNA probe to screen the gene bank. The construction of this critical DNA probe was initiated by the isolation of M-7 toxin crystals fron a culture of B.t.sd.

The recovered M-7 toxin crystals were purified by standard procedures and then digested with trypsin to produce peptide fragments. The amino acid sequences of several of these tryptic fragments was determined by standard procedures. Subsequently, after selection of certain sequences, a probe was chemically synthesized by known means. The resulting probe was labelled and hybridized by procedures known in the art. The net result was the detection of positive clones, i.e., those that hybridized to the constructed probe.

A representative of the positive clones was subjected to a western blot using rabbit anti M-7 crystal antiserum developed by standard procedures. Confirmation of the success of the cloning and expression of M-7 toxin was obtained when a positive reaction was observed with the positive clone and the antibody against M-7 toxin crystal.

The recombinant plasmids isolated from representative positive clones were found to have a 5.8 kb DNA fragment inserted into the BamHI site. This 5.8 kb DNA fragment was excised from a representative positive clone (pCH-B 3) with BamHI, purified, and then subcloned into the BamHI site of the known and available plasmid pRO1614 (J. Bact. [1982]150:60; U.S. Pat. No. 4,374,200). Plasmid pRO1614 is available from the Northern Regional Research Laboratory, address below, where its deposit number is NRRL B-12127. The plasmid is derived from pBR322 and has unique HindIII, BamHI, and SalI and PvuII restriction sites; a PstI insertion includes the carbenicillin resistance gene and a *P. aeruginosa* replication system. *Pseudomonas fluorescens* was transformed with this constructed shuttle vector and the expression of M-7 toxin was verified by its identification on a western blot.

Plasmid pCH-B3, or plasmid PRO1614 with the 5.8 kb fragment insert, can be recovered from their bacterial hosts by well-known procedures, e.g., using the cleared lysate-isopycnic density gradient procedures. If desired, the 5.8 kb fragment can be excised from pRO1614 by digestion with BamHI and cloned into a different vector for transformation into another host. These procedures are all well known to persons skilled in the art.

Plasmid pCH-B3, in an *E. coli* host, was deposited with the ARS Patent Collection, Culture Collection Research-Fermentation Laboratory, Northern Regional Research Center, Peoria, Ill. 61604. The deposit was made in the permanent collection of the repository to be maintained by the repository for at least 30 years. The deposit was made on July 18, 1985, and given the accession number NRRL B-15981. A subculture is available to the public upon the grant of a patent disclosing the deposit. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

The toxin gene of the subject invention can be introduced into a wide variety of microbial hosts. Expression of the toxin gene (M-7) results, directly or indirectly, in the intracellular production and maintenance of the pesticide. With suitable hosts, e.g., Pseudomonas, the microbes can be applied to the situs of beetles of the order Coleoptera where they will proliferate and be ingested by the susceptible beetles. The result is a control of the unwanted beetles. Alternatively, the microbe hosting the toxin M-7 gene can be treated under conditions that prolong the activity of the toxin produced in the cell. The treated cell then can be applied to the environment of target pest(s). The resulting product retains the toxicity of the M-7 toxin.

Where the M-7 toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, peroxide for stable maintenance and expression of the gene expressing the polypeptide pesticide, and, desirably, provide for improved protection of the pesticide from environmental degradation and inactivation.

A large number of microorganisms are known to inhabit the phylloplane (the surface of plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Xanthomonas, Streptomyces, Rhizobium, Rhodopseudomonas, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas, spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the M-7 gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will occur only after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop condon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct or may be combined as a separate DNA fragment with the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide protrophy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin producing host, so that it may effectively compete with the wild-type microorganisms and stably occupy a niche in the environment of the vegetation to be protected.

Where no functional replication system is present, the construct will also include a sequence of at least 50 bp, preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that the toxin gene is lost, the resulting organism will be likely to also lose the complementing gene and/or the gene providing for the competitive advantage, so that it will be unable to complete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898; 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element usually present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270; 4,362,817; and 4,371,625.

The M-7 gene can be introduced between the transcriptional and translational initiation region and the transcriptional and translational termination region, so as to be under the regulatory control of the initiation region. This construct wil be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Preferred hosts, particularly those in the phytosphere, will have certain characteristics which enhance the environmental stability of the toxins in the host. Protective qualities include a low level of proteolytic degradtion, thick cell walls, pigmentation, and the like. Other characteristics of interest for the host include leaf affinity, lack of mammalian toxicity, attractiveness to pests for ingestion, ease of handling and storage, rate of proliferation in the field, competitiveness, and the like.

In the field applications, the transformant strain will be applied to its natural habitat, such as the rhizosphere or phylloplane of the plant to be protected from the pest. The transformant strain will grow in its natural habitat, while producing the M-7 toxin which will be absorbed and/or ingested by the larvae or adult pest, or have a toxic effect on the ova. The persistence of the microorganisms will provide for long-term protection of the vegetation, although repetitive administrations may be required from time to time. The organism may be applied by spraying, soaking, injection into the soil, seed coating, seedling coating or spraying, or the like. Where administered in the field, generally concentrations of the organism will be from $10^6$ to $10^{10}$ cells/ml, and the volume applied per hectare will be generally from about 0.1 oz to 2 lbs or more. Where administered to a plant part, the concentration of the organism will usually be from $10^3$ to $10^6$ cells/cm$^2$.

Suitable host cells, where the pesticide-containing cells will be treated to prolong the activity of the toxin in the cell when the then dead cell is applied to the environment of target pest(s), may include either prokaryotes or eukaryotes, normally being limited to those cells which do not provide substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nirobacteraceae. Among eukaryotes are fungi, such as Phycomycetes and Ascomycetes, which include yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the M-7 gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when killed, rather than in a spore form, although in some instances spores may be employed.

The cells may be inhibited from proliferation in a variety of ways, so long as the technique does not deleteriously affect the properties of the pesticide, nor diminish the cellular capability in protecting the pesticide. The techniques may involve physical treatment, chemical treatment, changing the physical character of the cell substantially intact, or the like.

Various techniques for inactivating the host cells include heat, usually 50° C. to 70° C.; freezing; UV ifrradiation, lyophilization; toxins, e.g., antibiotics; phenols; anilides, e.g., carbanilide and salicylanilide; hydroxyurea; quaternaries; alcohols; antibacterial dyes; EDTA and amidines; non-specific organic and inorganic chemicals, such as halogenating agents, e.g., chlorinating, brominating or iodinating agents; aldehydes, e.g., glutaraldehyde or formaldehyde; toxic gases, such as ozone and ethylene oxide; peroxide; psoralens; desiccating agents or the like, which may be used individually or in combination. The choice of agent will depend upon the particular pesticide, the nature of the host cell, the nature of the modification of the cellular structure, such as fixing and preserving the cell wall with crosslinking agents, or the like.

The cells generally will have enhanced structural stability which will enhance resistance to environmental degradation in the field. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The cellular host containing the M-7 pesticidal gene may be grown in any convenient nutrient medium, where the DNA construct provides a selective advantage, providing for a selective medium so that substantially all or all of the cells retain the M-7 gene. These cells may then be harvested in accordance with conventional ways. Alternatively, the cells can be fixed prior to harvesting.

The method of treating the host organism containing the toxin can fulfill a number of functions. First, it may enhance structural integrity. Second, it may provide for enhanced proteolytic stability of the toxin, by modifying the toxin so as to reduce its suceptibility to proteolytic degradation and/or by reducing the proteolytic activity of proteases naturally present in the cell. The cells are preferably modified at an intact stage and when there has been a substantial buildup of the toxin protein. These modifications can be achieved in a variety of ways, such as by using chemical reagents having a broad spectrum of chemical reactivity. The intact cells can be combined with a liquid reagent medium containing the chemical reagents, with or without agitation, at temperatures in the range of about −10 to 60° C. The reaction time may be determined empirically and will vary widely with the reagents and reaction conditions. Cell concentrations will vary from about $10^2$ to $10^{10}$ per ml.

Of particular interest as chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropanol and ethanol; various histologic fixatives, such as Bouin's fixative and Helly's fixative (see Humason, Gretchen L., Animal Tissue Techniques, W. H. Freeman and Company, 1967); or a combination of physical (heat) and chemical agents that prolong the activity of the toxin produced in the cell when the cell is applied to the environment of the target pest(s).

For halogenation with iodine, temperatures will generally range from about 0° to 50° C., but the reaction can be conveniently carried out at room temperature. Conveniently, the iodination may be performed using triiodide or iodine at 0.5 to 5% in an acidic aqueous medium, particularly an aqueous carboxylic acid solution that may vary from about 0.5-5M. Conveniently, acetic acid may be used, although other carboxylic acids, generally of from about 1 to 4 carbon atoms, may also be employed. The time for the reaction will generally range from less than a minute to about 24 hr, usually from about 1 to 6 hr. Any residual iodine may be removed by reaction with a reducing agent, such as dithionite, sodium thiosulfate, or other reducing agent compatible with ultimate usage in the field. In addition, the modified cells may be subjected to further treatment, such as washing to remove all of the reaction medium, isolation in dry form, and formulation with typical stickers, spreaders, and adjuvants generally utilized in agricultural applications, as is well known to those skilled in the art.

Of particular interest are reagents capable of crosslinking the cell wall. A number of reagents are known in the art for this purpose. The treatment should result in enhanced stability of the pesticide. That is, there shold be enhanced persistence or residual activity of the pesticide under field conditions. Thus, under conditions where the pesticidal activity of untreated cells diminishes, the activity of treated cells remains for periods of from 1 to 3 times longer.

The cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueousbased or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest(s), e.g., plants, soil or water, by spraying, dusting, sprinkling or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B. thuringiensis* strain *san diego* NRRL B-15939

A subculture or starter culture of *B. thuringiensis* strain *san diego* NRRL B-15939 can be used to inoculate the following medium, known as LB broth:

| | |
|---|---|
| Tryptone | 10 gm |
| Yeast extract | 5 gm |
| NaCl | 5 gm |
| 5N NaOH | 0.6 ml |
| Water | 1000 ml |

As per standard microbiological techniques, the above medium would be sterilized prior to inoculation and the inoculations would be done using aseptic procedures. The M-7 cells are grown for 3-4 days at 30° C.

A detailed procedure is as follows:

A series of 150 ml Erlenmeyer flasks containing sterile PWYE medium (peptone 5.0%; yeast extract 0.1%; NaCl 0.55 in 1 liter of water; adjust pH to 7.5) are inoculated from a petri plate culture of B. thuringiensis strain san diego, NRRL B-15939. The flasks are incubated at 30° C. on a rotary shaker (200 rpm) overnight. From this starter culture, 300 ml of LB broth in a 2-liter flask is inoculated using 7.5 ml of the starter. The LB-broth flasks are incubated under the same conditions as the starter, but are harvested after 4 days.

The above procedure can be readily scaled up to large fermentors by procedures well known in the art.

The Bt spores and crystals, obtained in the above fermentation, can be isolated by procedures well known in the art. A frequently-used procedure is to subject the harvested fermentation broth to separation techniques, e.g., centrifugation.

EXAMPLE 2

Cloning and Epression of M-7 Toxin Gene

Total DNA (chromosomal and plasmid) was isolated from the M-7 cells of Example 1 and purified by standard procedures. The resulting purified DNA was digested with the restriction endonuclease BamHI, using the supplier's instruction. The digested DNA was then cloned into the BamHI site of the well-known plasmid pBR322 to give a gene bank of M-7 DNA. This cloning procedure was done following standard well-known procedures.

A DNA probe to screen the gene bank was obtained as follows: M-7 crystals were isolated from a culture grown in NYSM medium (10 gm tryptone, 5 gm NaCl, 5 gm yeast extract, 2 gm $MgSO_4 \cdot 7H_2O$, 1000 ml water, pH 7.5) overnight at 30° C. The purified crystals were dissolved in 8 M urea, 0.1 M glycine, pH 8.2 and digested with trypsin overnight at room temperature. The resulting peptide fragments were separated on a C4 reverse phase high pore column with a 180 min gradient of 91% solution A (0.1% trifluoroacetic acid in $H_2O$) to 40% solution A in 0.1% trifluoroacetic acid in acetonitrile. The aminoacid sequences of several tryptic fragments were obtained and a sequence of 6 aminoacids were selected for synthesis of a mixed probe, 17 bases in length, with a redundancy of 32.

The probe was end-labeled with polynucleotide kinase and [$\gamma$-$^{32}$P]ATP and hybridized to bacterial colonies containing recombinant plasmids as constructed for the M-7 gene bank. The colony filters were prepared according to Hanahan and Meselson (1980) Gene 10:63-67. Positive colonies were identified by autoradiography. The recombinant plasmids isolated from seven positive clones (pCH-B3 as representative) were found to have a 5.8 kb (kilobase pairs) DNA fragment inserted into the BamHI site.

A western blot (Burnette, W. N. [1981] Anal. Biochem. 112:195) of pCH-B3 was performed on an SDS-PAGE of an overnight culture, using rabbit anti-M-7 crystal antiserum. A protein of about 86 kilodalton was identified. The clone pCH-B3, therefore, contains an M-7 DNA fragment that encodes for a protein having serological identity with the protein from the M-7 crystals. The recombinant protein may be bigger than the toxin from solubilized M-7 crystals because of unavailability of transcriptional and/or translational stop signals in the given plasmid construction.

The nucleotide sequence encoding the B.t.sd toxin gene is shown in table A. The deduced amino acid sequence is shown in Table B.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G — guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M — A, C or T The above shows that the novel amino acid sequence of the M7 toxin, and other useful proteins, can be prepared by equivalent nucleotide sequences encoding the same amino acid sequence of the proteins. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

EXAMPLE 3

Production of M-7 Toxin Protein by Clone pCH-B3

A 20 liter culture of pCH-B3 (L-broth with 70 μg/ml Ampicillin) was grown in a fermenter and harvested at OD600 = 3.35. The cell pellet was washed with water and resuspended in 500 ml glycine buffer (0.1 M glycine, pH 8.0 with tris base) containing 2 g lysozyme, 1 mM PMSF (phenylmethylsulfonyl fluoride), 1 mM TPCK (1-tosylamide-2-phenyl ethylchloromethyl ketone), and 500 μg DNase I and incubated at room temperature for 30 min. The pH was then raised to 10 with NaOH and the cells were further ruptured in a bead beater (Biospec Products, Bartlesville, Okla.) on ice with four 30 second bursts 5 min apart. The extract was then centrifuged at 10,000 × g for 30 min.

EXAMPLE 4

Isolation and Purification of M-7 Toxin Proteom Produced by Clone pCH-B3

The protein from pCH-B3 was purified using affinity chromatography (Cuatrecasa, P. and Anfinsen, C. B. [1971] Meth. Enzymology Vol. 22 [ed. W. B. Jacoby]Acad. Press, N.Y.) as follows: Sepharose was activated with cyanogen bromide as described by Cuatrecasa and Anfinsen. Rabbit anti-M-7 crystal serum was added to the activated Sepharose and incubated overnight at room temperature with constant agitation. The affinity resign was then washed with 1% ethanolamine, 3 M NaCl, pH 9.2, and then with TBS (0.02 M tris-HCl, 0.07 M NaCl, pH 7.5) containing 0.02% sodium azide. The column was equilibrated in 0.1 M glycine pH 10 (with tris base) containing 1 mM EDTA (ethylenediaminetetraacetic acid), 1 mM PMSF, 1 mM TPCK, and 0.02% sodium azide. The E. coli extract, prepared above, was loaded onto the column and recirculated for 64 hr at 4° C. The extract was washed from the column with 1 M NaCl and 0.1 M glycine-tris pH 10, and the bound M-7 toxin was removed from the column with 3 M sodium perchlorate, 0.1 M glycine-tris pH 10. The M-7 toxin was then dialyzed against water and concentrated (MicroPro D: Con, Pierce Chem., Co., Rockford, Ill.).

The purified M-7 toxin can be administered (applied) to vegetation susceptible to infestation by bettles of the order Coleoptera to protect the vegetation. Advantageously, the M-7 toxin will be made environmentally stable by use of suitable coatings well known to persons skilled in the art.

EXAMPLE 5

Subcloning and Expression of M-7 Toxin Gene into *Pseudomonas Fluorescens*

The 5.8 kb DNA fragment carrying the M-7 toxin gene was excised from plasmid pCH-B3 with BamHI, purified, and subcloned into the BamHI site of the plasmid pRO1614. *Pseudomonas fluorescens* was transformed with this plasmid. The expression of M-7 toxin by recombinant Pseudomonas cells was verified by its identification on a western blot.

EXAMPLE 6

Testing of *B. thuringiensis* strain *san diego* NRRL B-15939 Spores and Crystal

*B. thuringiensis* strain san diego NRRL B-15939 spores and crystal, obtained as described above, were tested against various insects. The insect species tested and a summary of the results are listed in Table 1.

The method used to test for *D. undecimpunctata* (WSCB) activity consisted of spraying a spore/crystal suspension onto leaf discs of lettuce in a spray tower apparatus. (The larvae of this species are reared on lettuce leaves.) The spray was dried in a laminar flow hood and placed in a container on moist filter paper. Ten larvae of WSCB were added and the containers were incubated at 25° C. and 14 hr photoperiod. Fresh treated discs were added as needed. Inhibition of feeding was noted and mortality was recorded at 5 and 7 days. Results of 2 bioassays are given in Table 2.

In order to test the M-7 toxin for activity against *Pyrrhalta luteola* (elm leaf beetle), a suspension of solubilized protein from M-7 crystals was applied to elm leaves. The dried leaves were then placed in a container on moist sand. Five to ten larvae of P. luteola were added and the containers were incubated at room temperature. Mortality was recorded at 3 and 5 days. An $LC_{50}$ of 120 ng toxin/cm$^2$ of leaf surface was calculated from these assays.

TABLE A

Nucleotide Sequence Encoding the *Bacillus thuringiensis* strain *san diego* Toxin Gene

|  |  |  |  |  |
|---|---|---|---|---|
|  |  |  | ATGA | ATCCGAACAA |
| TCGAAGTGAA | CATGATACAA | TAAAAACTAC | TGAAAATAAT | GAGGTGCCAA |
| CTAACCATGT | TCAATATCCT | TTAGCGGAAA | CTCCAAATCC | AACACTAGAA |
| GATTTAAATT | ATAAAGAGTT | TTTAAGAATG | ACTGCAGATA | ATAATACGGA |
| AGCACTAGAT | AGCTCTACAA | CAAAAGATGT | CATTCAAAAA | GGCATTTCCG |
| TAGTAGGTGA | TCTCCTAGGC | GTAGTAGGTT | TCCCGTTTGG | TGGAGCGCTT |
| GTTTCGTTTT | ATACAAACTT | TTTAAATACT | ATTTGGCCAA | GTGAAGACCC |
| GTGGAAGGCT | TTTATGGAAC | AAGTAGAAGC | ATTGATGGAT | CAGAAAATAG |
| CTGATTATGC | AAAAAATAAA | GCTCTTGCAG | AGTTACAGGG | CCTTCAAAAT |
| AATGTCGAAG | ATTATGTGAG | TGCATTGAGT | TCATGGCAAA | AAAATCCTGT |
| GAGTTCACGA | AATCCACATA | GCCAGGGGCG | GATAAGAGAG | CTGTTTTCTC |
| AAGCAGAAAG | TCATTTTCGT | AATTCAATGC | CTTCGTTTGC | AATTTCTGGA |
| TACGAGGTTC | TATTTCTAAC | AACATATGCA | CAAGCTGCCA | ACACACATTT |
| ATTTTTACTA | AAAGACGCTC | AAATTTATGG | AGAAGAATGG | GGATACGAAA |
| AAGAAGATAT | TGCTGAATTT | TATAAAAGAC | AACTAAAACT | TACGCAAGAA |
| TATACTGACC | ATTGTGTCAA | ATGGTATAAT | GTTGGATTAG | ATAAATTAAG |
| AGGTTCATCT | TATGAATCTT | GGGTAAACTT | TAACCGTTAT | CGCAGAGAGA |
| TGACATTAAC | AGTATTAGAT | TTAATTGCAC | TATTTCCATT | GTATGATGTT |
| CGGCTATACC | CAAAAGAAGT | TAAAACCGAA | TTAACAAGAG | ACGTTTTAAC |
| AGATCCAATT | GTCGGAGTCA | ACAACCTTAG | GGGCTATGGA | ACAACCTTCT |
| CTAATATAGA | AAATTATATT | CGAAAACCAC | ATCTATTTGA | CTATCTGCAT |
| AGAATTCAAT | TTCACACGCG | GTTCCAACCA | GGATATTATG | GAAATGACTC |
| TTTCAATTAT | TGGTCCGGTA | ATTATGTTTC | AACTAGACCA | AGCATAGGAT |
| CAAATGATAT | AATCACATCT | CCATTCTATG | GAAATAAATC | CAGTGAACCT |
| GTACAAAATT | TAGAATTTAA | TGGAGAAAAA | GTCTATAGAG | CCGTAGCAAA |
| TACAAATCTT | GCGGTCTGGC | CGTCCGCTGT | ATATTCAGGT | GTTACAAAAG |
| TGGAATTTAG | CCAATATAAT | GATCAAACAG | ATGAAGCAAG | TACACAAACG |
| TACGACTCAA | AAAGAAATGT | TGGCGCGGTC | AGCTGGGATT | CTATCGATCA |
| ATTGCCTCCA | GAAACAACAG | ATGAACCTCT | AGAAAAGGGA | TATAGCCATC |
| AACTCAATTA | TGTAATGTGC | TTTTTAATGC | AGGGTAGTAG | AGGAACAATC |
| CCAGTGTTAA | CTTGGACACA | TAAAAGTGTA | GACTTTTTTA | ACATGATTGA |
| TTCGAAAAAA | ATTACACAAC | TTCCGTTAGT | AAAGGCATAT | AAGTTACAAT |
| CTGGTGCTTC | CGTTGTCGCA | GGTCCTAGGT | TTACAGGAGG | AGATATCATT |
| CAATGCACAG | AAAATGGAAG | TGCGGCAACT | ATTTACGTTA | CACCGGATGT |
| GTCGTACTCT | CAAAAATATC | GAGCTAGAAT | TCATTATGCT | TCTACATCTC |
| AGATAACATT | TACACTCAGT | TTAGACGGGG | CACCATTTAA | TCAATACTAT |
| TTCGATAAAA | CGATAAATAA | AGGAGACACA | TTAACGTATA | ATTCATTTAA |
| TTTAGCAAGT | TTCAGCACAC | CATTCGAATT | ATCAGGGAAT | AACTTACAAA |
| TAGGCGTCAC | AGGATTAAGT | GCTGGAGATA | AAGTTTATAT | AGACAAAATT |
| GAATTTATTC | CAGTGAAT |  |  |  |

TABLE B

Deduced Amino Acid Sequence of *Bacillus thuringiensis* strain *san diego* Toxin

|  |  |  |  |
|---|---|---|---|
| 5 | 10 | 15 | 20 |
| Met Asn Pro Asn Asn | Arg Ser Glu His Asp | Thr Ile Lys Thr Thr | Glu Asn Asn Glu Val |
| 25 | 30 | 35 | 40 |
| Pro Thr Asn His Val | Gln Tyr Pro Leu Ala | Glu Thr Pro Asn Pro | Thr Leu Glu Asp Leu |
| 45 | 50 | 55 | 60 |
| Asn Tyr Lys Glu Phe | Leu Arg Met Thr Ala | Asp Asn Asn Thr Glu | Ala Leu Asp Ser Ser |
| 65 | 70 | 75 | 80 |
| Thr Thr Lys Asp Val | Ile Gln Lys Gly Ile | Ser Val Val Gly Asp | Leu Leu Gly Val Val |
| 85 | 90 | 95 | 100 |
| Gly Phe Pro Phe Gly | Gly Ala Leu Val Ser | Phe Tyr Thr Asn Phe | Leu Asn Thr Ile Trp |
| 105 | 110 | 115 | 120 |
| Pro Ser Glu Asp Pro | Trp Lys Ala Phe Met | Glu Gln Val Glu Ala | Leu Met Asp Gln Lys |
| 125 | 130 | 135 | 140 |
| Ile Ala Asp Tyr Ala | Lys Asn Lys Ala Leu | Ala Glu Leu Gln Gly | Leu Gln Asn Asn Val |
| 145 | 150 | 155 | 160 |
| Glu Asp Tyr Val Ser | Ala Leu Ser Ser Trp | Gln Lys Asn Pro Val | Ser Ser Arg Asn Pro |
| 165 | 170 | 175 | 180 |
| His Ser Gln Gly Arg | Ile Arg Glu Leu Phe | Ser Gln Ala Glu Ser | His Phe Arg Asn Ser |
| 185 | 190 | 195 | 200 |
| Met Pro Ser Phe Ala | Ile Ser Gly Tyr Glu | Val Leu Phe Leu Thr | Thr Tyr Ala Gln Ala |
| 205 | 210 | 215 | 220 |
| Ala Asn Thr His Leu | Phe Leu Leu Lys Asp | Ala Gln Ile Tyr Gly | Glu Glu Trp Gly Tyr |
| 225 | 230 | 235 | 240 |
| Glu Lys Glu Asp Ile | Ala Glu Phe Tyr Lys | Arg Gln Leu Lys Leu | Thr Gln Gln Tyr Thr |
| 245 | 250 | 255 | 260 |
| Asp His Cys Val Lys | Trp Tyr Asn Val Gly | Leu Asp Lys Leu Arg | Gly Ser Ser Tyr Glu |
| 265 | 270 | 275 | 280 |
| Ser Trp Val Asn Phe | Asn Arg Tyr Arg Arg | Glu Met Thr Leu Thr | Val Leu Asp Leu Ile |
| 285 | 290 | 295 | 300 |

TABLE B-continued

Deduced Amino Acid Sequence of *Bacillus thuringiensis* strain *san diego* Toxin

| | | | |
|---|---|---|---|
| Ala Leu Phe Pro Leu 305 | Tyr Asp Val Arg Leu 310 | Tyr Pro Lys Glu Val 315 | Lys Thr Glu Leu Thr 320 |
| Arg Asp Val Leu Thr 325 | Asp Pro Ile Val Gly 330 | Val Asn Asn Leu Arg 335 | Gly Tyr Gly Thr Thr 340 |
| Phe Ser Asn Ile Glu 345 | Asn Tyr Ile Arg Lys 350 | Pro His Leu Phe Asp 355 | Tyr Leu His Arg Ile 360 |
| Gln Phe His Thr Arg 365 | Phe Gln Pro Gly Tyr 370 | Tyr Gly Asn Asp Ser 375 | Phe Asn Tyr Trp Ser 380 |
| Gly Asn Tyr Val Ser 385 | Thr Arg Pro Ser Ile 390 | Gly Ser Asn Asp Ile 395 | Ile Thr Ser Pro Phe 400 |
| Tyr Gly Asn Lys Ser 405 | Ser Glu Pro Val Gln 410 | Asn Leu Glu Phe Asn 415 | Gly Glu Lys Val Tyr 420 |
| Arg Ala Val Ala Asn 425 | Thr Asn Leu Ala Val 430 | Trp Pro Ser Ala Val 435 | Tyr Ser Gly Val Thr 440 |
| Lys Val Glu Phe Ser 445 | Gln Tyr Asn Asp Gln 450 | Thr Asp Glu Ala Ser 455 | Thr Gln Thr Tyr Asp 460 |
| Ser Lys Arg Asn Val 465 | Gly Ala Val Ser Trp 470 | Asp Ser Ile Asp Gln 475 | Leu Pro Pro Glu Thr 480 |
| Thr Asp Glu Pro Leu 485 | Glu Lys Gly Tyr Ser 490 | His Gln Leu Asn Tyr 495 | Val Met Cys Phe Leu 500 |
| Met Gln Gly Ser Arg 505 | Gly Thr Ile Pro Val 510 | Leu Thr Trp Thr His 515 | Lys Ser Val Asp Phe 520 |
| Phe Asn Met Ile Asp 525 | Ser Lys Lys Ile Thr 530 | Gln Leu Pro Leu Val 535 | Lys Ala Tyr Lys Leu 540 |
| Gln Ser Gly Ala Ser 545 | Val Val Ala Gly Pro 550 | Arg Phe Thr Gly Gly 555 | Asp Ile Ile Gln Cys 560 |
| Thr Glu Asn Gly Ser 565 | Ala Ala Thr Ile Tyr 570 | Val Thr Pro Asp Val 575 | Ser Tyr Ser Gln Lys 580 |
| Tyr Arg Ala Arg Ile 585 | His Tyr Ala Ser Thr 590 | Ser Gln Ile Thr Phe 595 | Thr Leu Ser Leu Asp 600 |
| Gly Ala Pro Phe Asn 605 | Gln Tyr Tyr Phe Asp 610 | Lys Thr Ile Asn Lys 615 | Gly Asp Thr Leu Thr 620 |
| Tyr Asn Ser Phe Asn 625 | Leu Ala Ser Phe Ser 630 | Thr Pro Phe Glu Leu 635 | Ser Gly Asn Asn Leu 640 |
| Gln Ile Gly Val Thr Ile Pro Val Asn | Gly Leu Ser Ala Gly | Asp Lys Val Tyr Ile | Asp Lys Ile Glu Phe |

TABLE 1

Insects Evaluated for Susceptibility to *Bacillus thuringiensis* strain *san diego*

| Order | Family | Species | Common Name | Stages Tested | Activity |
|---|---|---|---|---|---|
| Coleoptera | Chrysomelidae | Diabrotica undecimpunctata | Western spotted cucumber beetle | Adult, larva | + |
| | | Pyrrhalta luteola | Elm leaf beetle | Adult, larva | ++++ |
| | | Haltica tombacina | — | Adult, larva | +++ |
| | Curculionidae | Otiorhynchus sulcatus | Black vine weevil | Larva | ++ |
| | Tenebrionidae | Tenebrio molitor | Yellow mealworm | Larva | ++ |
| | | Tribolium castaneum | Red flour beetle | Adult, larva | — |
| | Dermestidae | Attagenus megatoma | — | Larva | — |
| | Ptinidae | Gibbium psylloides | — | Adult | — |
| Diptera | Culicidae | Aedes aegypti | Yellow fever mosquito | Larva | — |
| Lepidoptera | Noctuidae | Spodoptera exigua | Beet armyworm | Larva | — |
| | | Trichoplusia ni | Cabbage looper | Larva | — |

TABLE 2

Results of 2 Bioassays of *Bacillus thuringiensis* M-7 Against Second Instar *Diabrotica undecimpunctata U.* at 7 Days Post-Inoculation

| Treatment | Avg. no. leaf discs consumed/rep. | % Mortality |
|---|---|---|
| Exp 1 Control | 3 | 7.5 ± 15.0 |
| 4.3 × 10⁷ spores/ml | <1 | 27.5 ± 9.6 |
| 4.3 × 10⁸ spores/ml | 0 | 62.5 ± 26.3 |
| Exp 2 Control | 1 | 12.5 ± 12.6 |
| 1 × 10⁶ spores/ml | <1 | 30.0 ± 8.2 |
| 1 × 10⁷ spores/ml | 0 | 50.0 ± 21.6 |

We claim:

1. A host transformed by a recombinant DNA transfer vector comprising DNA coding for a protein toxin having the following amino acid sequence:

```
              5                  10                 15
Met Asn Pro Asn Asn Arg Ser Glu His Asp Thr Ile Lys Thr Thr 20                  25                 30
Glu Asn Asn Glu Val Pro Thr Asn His Val Gln Tyr Pro Leu Ala 35                  40                 45
Glu Thr Pro Asn Pro Thr Leu Glu Asp Leu Asn Tyr Lys Glu Phe 50                  55                 60
Leu Arg Met Thr Ala Asp Asn Asn Thr Glu Ala Leu Asp Ser Ser 65                  70                 75
Thr Thr Lys Asp Val Ile Gln Lys Gly Ile Ser Val Val Gly Asp 80                  85                 90
Leu Leu Gly Val Val Gly Phe Pro Phe Gly Gly Ala Leu Val Ser 95                 100                105
Phe Tyr Thr Asn Phe Leu Asn Thr Ile Trp Pro Ser Glu Asp Pro 110                 115                120
Trp Lys Ala Phe Met Glu Gln Val Glu Ala Leu Met Asp Gln Lys 125                 130                135
Ile Ala Asp Tyr Ala Lys Asn Lys Ala Leu Ala Glu Leu Gln Gly 140                 145                150
Leu Gln Asn Asn Val Glu Asp Tyr Val Ser Ala Leu Ser Ser Trp 155                 160                165
Gln Lys Asn Pro Val Ser Ser Arg Asn Pro His Ser Gln Gly Arg 170                 175                180
Ile Arg Glu Leu Phe Ser Gln Ala Glu Ser His Phe Arg Asn Ser 185                 190                195
Met Pro Ser Phe Ala Ile Ser Gly Tyr Glu Val Leu Phe Leu Thr 200                 205                210
Thr Tyr Ala Gln Ala Ala Asn Thr His Leu Phe Leu Leu Lys Asp 215                 220                225
Ala Gln Ile Tyr Gly Glu Glu Trp Gly Tyr Glu Lys Glu Asp Ile 230                 235                240
Ala Glu Phe Tyr Lys Arg Gln Leu Lys Leu Thr Gln Glu Tyr Thr 245                 250                255
Asp His Cys Val Lys Trp Tyr Asn Val Gly Leu Asp Lys Leu Arg 260                 265                270
Gly Ser Ser Tyr Glu Ser Trp Val Asn Phe Asn Arg Tyr Arg Arg 275                 280                285
Glu Met Thr Leu Thr Val Leu Asp Leu Ile Ala Leu Phe Pro Leu 290                 295                300
Tyr Asp Val Arg Leu Tyr Pro Lys Glu Val Lys Thr Glu Leu Thr 305                 310                315
Arg Asp Val Leu Thr Asp Pro Ile Val Gly Val Asn Asn Leu Arg 320                 325                330
Gly Tyr Gly Thr Thr Phe Ser Asn Ile Glu Asn Tyr Ile Arg Lys 335                 340                345
Pro His Leu Phe Asp Tyr Leu His Arg Ile Gln Phe His Thr Arg 350                 355                360
Phe Gln Pro Gly Tyr Tyr Gly Asn Asp Ser Phe Asn Tyr Trp Ser 365                 370                375
Gly Asn Tyr Val Ser Thr Arg Pro Ser Ile Gly Ser Asn Asp Ile 380                 385                390
Ile Thr Ser Pro Phe Tyr Gly Asn Lys Ser Ser Glu Pro Val Gln 395                 400                405
Asn Leu Glu Phe Asn Gly Glu Lys Val Tyr Arg Ala Val Ala Asn 410                 415                420
Thr Asn Leu Ala Val Trp Pro Ser Ala Val Tyr Ser Gly Val-Thr 425                 430                435
Lys Val Glu Phe Ser Gln Tyr Asn Asp Gln Thr Asp Glu Ala Ser 440                 445                450
Thr Gln Thr Tyr Asp Ser Lys Arg Asn Val Gly Ala Val Ser Trp 455                 460                465
Asp Ser Ile Asp Gln Leu Pro Pro Glu Thr Thr Asp Glu Pro Leu 470                 475                480
Glu Lys Gly Tyr Ser His Gln Leu Asn Tyr Val Met Cys Phe Leu 485                 490                495
Met Gln Gly Ser Arg Gly Thr Ile Pro Val Leu Thr Trp Thr His 500                 505                510
Lys Ser Val Asp Phe Phe Asn Met Ile Asp Ser Lys Lys Ile Thr 515                 520                525
Gln Leu Pro Leu Val Lys Ala Tyr Lys Leu Gln Ser Gly Ala Ser 530                 535                540
Val Val Ala Gly Pro Arg Phe Thr Gly Gly Asp Ile Ile Gln Cys 545                 550                555
Thr Glu Asn Gly Ser Ala Ala Thr Ile Tyr Val Thr Pro Asp Val 560                 565                570
Ser Tyr Ser Gln Lys Tyr Arg Ala Arg Ile His Tyr Ala Ser Thr 575                 580                585
Ser Gln Ile Thr Phe Thr Leu Ser Leu Asp Gly Ala Pro Phe Asn 590                 595                600
Gln Tyr Tyr Phe Asp Lys Thr Ile Asn Lys Gly Asp Thr Leu Thr 605                 610                615
Tyr Asn Ser Phe Asn Leu Ala Ser Phe Ser Thr Pro Phe Glu Leu 620                 625                630
Ser Gly Asn Asn Leu Gln Ile Gly Val Thr Gly Leu Ser Ala Gly 635                 640
Asp Lys Val Tyr Ile Asp Lys Ile Glu Phe Ile Pro Val Asn
``` and variations thereof, wherein, the biological activity is retained.

* * * * *

UNITED STATES PATENT AND TRADEMARK OFFICE
CERTIFICATE OF CORRECTION

PATENT NO. : 4,853,331

DATED : August 1, 1989

INVENTOR(S) : Corinna Herrnstadt and Edward Wilcox

It is certified that error appears in the above-identified patent and that said Letters Patent is hereby corrected as shown below:

| | | |
|---|---|---|
| Column 2: | line 64: | "(pCH-B 3)" should read --(pCH-B3)-- |
| Column 3: | line 9: | "PRO1614" should read --pRO1614-- |
| Column 3: | line 58: | "peroxide" should read --provide-- |
| Column 5: | line 63: | "usually" should read --normally-- |
| Column 7: | line 1: | "Nirobacteraceae." should read --Nitrobacteraceae-- |
| Column 7: | line 44: | "ifrradiation," should read --irradiation-- |
| Column 8: | line 35: | "isopropanol" should read --isopropyl-- |
| Column 9: | line 61: | "NaCl10.55" should read --NaCl 0.5%-- |
| Column 10: | line 59: | "table A." should read --Table A-- |
| Column 12: | line 5: | "Proteom" should read --Protein-- |
| Column 12: | line 39: | "Fluorescens" should read --fluorescens-- |

Signed and Sealed this

Eighteenth Day of December, 1990

Attest:

HARRY F. MANBECK, JR.

Attesting Officer

Commissioner of Patents and Trademarks